United States Patent [19]
Filipi et al.

[11] Patent Number: 5,254,126
[45] Date of Patent: Oct. 19, 1993

[54] ENDOSCOPIC SUTURE PUNCH

[75] Inventors: Charles J. Filipi, Omaha, Nebr.; William C. McJames, II, Belle Mead; John Mandara, Jr., Piscataway, both of N.J.

[73] Assignee: Ethicon, Inc., Somerville, N.J.

[21] Appl. No.: 903,702

[22] Filed: Jun. 24, 1992

[51] Int. Cl.$^5$ .............................................. A61B 17/00
[52] U.S. Cl. ................................. 606/146; 606/139; 606/144; 606/148
[58] Field of Search ......................... 606/139, 144-148

[56] References Cited

U.S. PATENT DOCUMENTS

| | | |
|---|---|---|
| 3,470,875 | 10/1969 | Johnson .............................. 606/145 |
| 3,807,407 | 4/1974 | Schweizer ........................... 606/146 |
| 4,164,225 | 8/1979 | Johnson et al. ..................... 606/146 |
| 4,890,615 | 1/1990 | Caspari et al. . |
| 4,923,461 | 5/1990 | Caspari et al. . |
| 4,935,027 | 6/1990 | Yoon .................................. 606/148 |
| 4,957,498 | 9/1990 | Caspari et al. . |
| 5,088,979 | 2/1992 | Filipi et al. . |

Primary Examiner—Stephen C. Pellegrino
Assistant Examiner—Jeffrey A. Schmidt

[57] ABSTRACT

An endoscopic suture punch for use in endosurgical procedures, especially an anti-reflux procedure. This suture punch has an elongate frame and a handle mounted to one end of the frame. A pair of opposed jaws having tissue punches is mounted to the other end of the frame. One jaw is rigidly mounted to the frame while the other jaw is movably mounted to the frame, although both jaws can be movably mounted. An actuation handle is mounted to the frame for actuating the jaws. The suture punch has a suture pathway through the frame, the punches and the jaws for receiving the suture. There is a suture drive mechanism mounted to the frame for moving the suture through the suture pathway. The endoscopic suture punch is used with an invaginator for performing an anti-reflux procedure. The endoscopic suture punch may typically be used for suturing and other endoscopic procedures.

37 Claims, 9 Drawing Sheets

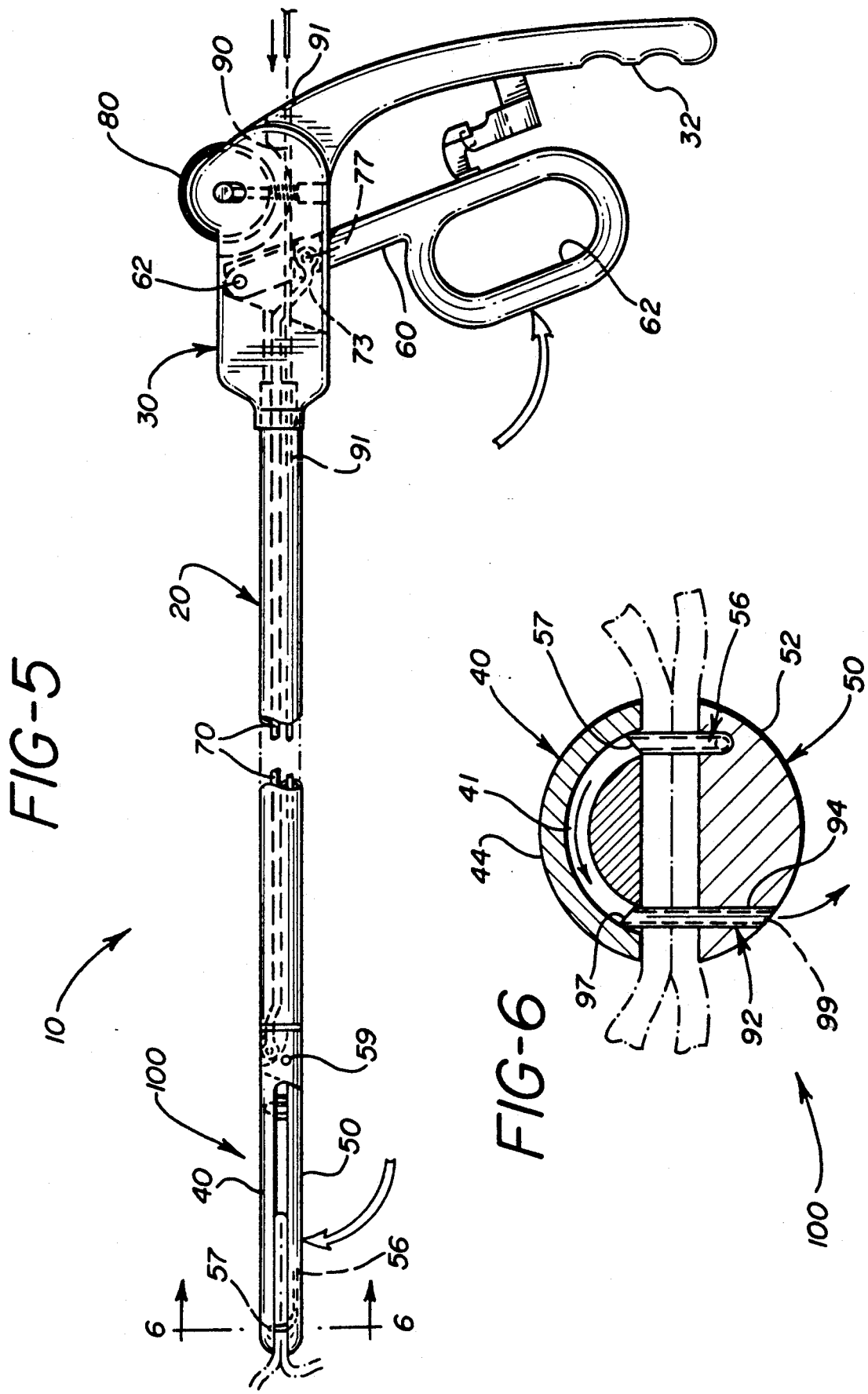

ENDOSCOPIC SUTURE PUNCH

TECHNICAL FIELD

The field of art to which this invention relates is surgical instrumentation, in particular endoscopic surgical instrumentation.

BACKGROUND ART

Endoscopic surgical procedures are gaining wide acceptance among surgeons and patients. There are many benefits associated with the use of endoscopic surgical procedures including reduced postoperative infection rate, reduced pain, decrease in both the post operative recuperative period and the duration of the hospital stay, and improved cosmesis. The term endoscopic as used herein is defined to include endoscopic, laparoscopic, thoracoscopic and arthroscopic, and, similar minimally invasive surgical techniques.

Numerous endoscopic surgical procedures have been developed including cholecystectomy, appendectomy and tubal ligation. Various types of endoscopic surgical instruments have been developed for use in these endoscopic procedures including endoscopic clip appliers, endoscopic sutures, endoscopes, endoscopic staplers, trocars, and trocar cannulas, and the like.

Although certain types of digestive disorders of the stomach are treatable with various types of pharmaceuticals, or changes in dietary habits, it is known that certain types of conditions are only responsive to surgical intervention. One such condition is intractable gastroesophageal reflux disease which typically involves the distal esophagus. A valvular mechanism exists at the junction of the esophagus and stomach which prevents acid from splashing up and entering the lower esophagus. When the fundus does not function properly, acid is allowed to splash into the esophagus. The symptoms of this condition include heartburn, regurgitation, dysphagia (difficult swallowing), chronic bronchitis in some, and chest pain. The conventional surgical remediation for this condition is known as an anti-reflux procedure. In the conventional anti-reflux procedure, an incision is initially made into the abdominal cavity. Once inside the abdomen, the surgeon completes the anti-reflux procedure by mobilizing the esophagus, then dividing the top short gastric vessels, and finally wrapping the fundus of the stomach around the distal esophagus. The wrap is secured with sutures. The purpose of this technique is to create a flap of stomach tissue about the esophagus that functions as a valve between the stomach and the esophagus, thereby preventing stomach acid from entering the lower esophagus. There is a need in the surgical field for such an anti-reflux operation performed using a minimally invasive endoscopic procedure. There is also a need in this art for endoscopic suturing instrumentation which can be used to perform endoscopic surgical procedures such as an endoscopic anti-reflux procedure.

SUMMARY OF THE INVENTION

An endoscopic suture punch for use in an anti-reflux procedure is disclosed. The suture punch comprises an elongate frame and a handle mounted to one end of the frame. A pair of opposed jaws having punch means is mounted to the other end of the frame. One jaw is rigidly mounted to the frame while the other jaw is movably mounted to the frame, although both jaws can be movably mounted. An actuation means is mounted to the frame for actuating the jaws. The suture punch has a suture pathway means through the frame, the punch means and the jaws for receiving a suture. There is a suture drive means mounted to the frame for moving the suture through the suture pathway. The endoscopic suture punch may typically be used for suturing in other endoscopic procedures.

Yet another aspect of the present invention is a combination comprising an endoscopic suture punch and an invaginator for performing an anti-reflux procedure. The invaginator comprises an elongate member having a tapered, blunt distal end. A tissue engaging means is extendable from said member proximal to said distal end. An actuating means for actuating said tissue engaging means is mounted to the proximal end of the elongate member. The endoscopic suture punch comprises an elongate frame. A handle is mounted to one end of said frame. A pair of opposed jaws is mounted to the other end of said frame. One jaw is rigidly mounted to the frame and the other jaw is movably mounted, although both jaws may be movably mounted. An actuation means is mounted to said frame for actuating the jaws. Punch means are mounted to said jaws for punching a suture pathway through tissue. And, there is a suture pathway means through said frame and jaws and punch means for receiving a suture. In addition, a suture drive means is mounted to the frame for moving the suture through the pathway means.

Yet another aspect of the present invention is a method of performing an endoscopic anti-reflux procedure on a mammal. The method comprises initially inserting the above-described invaginator into the esophagus of a mammal. Then, actuating the actuation means to engage the distal esophagus. Next, the distal end of the invaginator and the esophageal tissue engaged by the invaginator are displaced distally into the stomach to form an invaginated fold about the invaginator. The above-described endoscopic suture punch is inserted into the stomach through a trocar cannula, either before or after the invaginator is inserted into the esophagus. The distal end of the suture punch is positioned proximal to the distal end of the invaginator. The next step in the method requires the suturing of the invaginated fold by inserting the open jaws of the suture punch about the invaginated fold such that one jaw is external to the fold and one jaw is internal to the fold, and then actuating the actuation means such that the moveable jaw is moved to a closed position and the punch means form a pathway through the tissue of the invaginated fold. Then, a suture is fed through a suture pathway means and through the invaginated fold. A U-stitch is resultingly formed. The suture traverses a channel in the inside jaw and returns through another pathway to the external jaw where it then exits via an exit port. Then, the suture punch and both ends of the suture are withdrawn from the stomach leaving a section of the suture in the tissue pathway in the invaginated fold. Next a knot is tied to secure the suture about the invaginated fold. Finally, additional sutures are similarly inserted as needed.

Still another aspect of the present invention is a method of endoscopic suturing using the above-described endoscopic suture punch. The suture punch is inserted through a trocar cannula into a body cavity. The jaws of the punch are then opened and placed about tissue. Then, the jaws are actuated and closed about the tissue such that the punch means pierce a pathway through the tissue. Next, a conventional suture is fed through the suture pathway means, through the tissue and out through the endoscopic suture punch. A resultant U-stitch is formed in the tissue. Then, a conventional knot is secured in the suture about the tissue.

Other features and advantages of the invention will become more apparent from the following description and accompanying drawings.

BRIEF DESCRIPTION OF THE DRAWINGS

FIG. 5 is a side elevational view of the jaws of the endoscopic suture punch with the jaws actuated about tissue.

FIG. 6 is a cross-sectional view of the jaws showing the suture punch means and the pathway for the suture, taken along View Line 6—6 of FIG. 5.

BEST MODE FOR CARRYING OUT THE INVENTION

Figure 1:
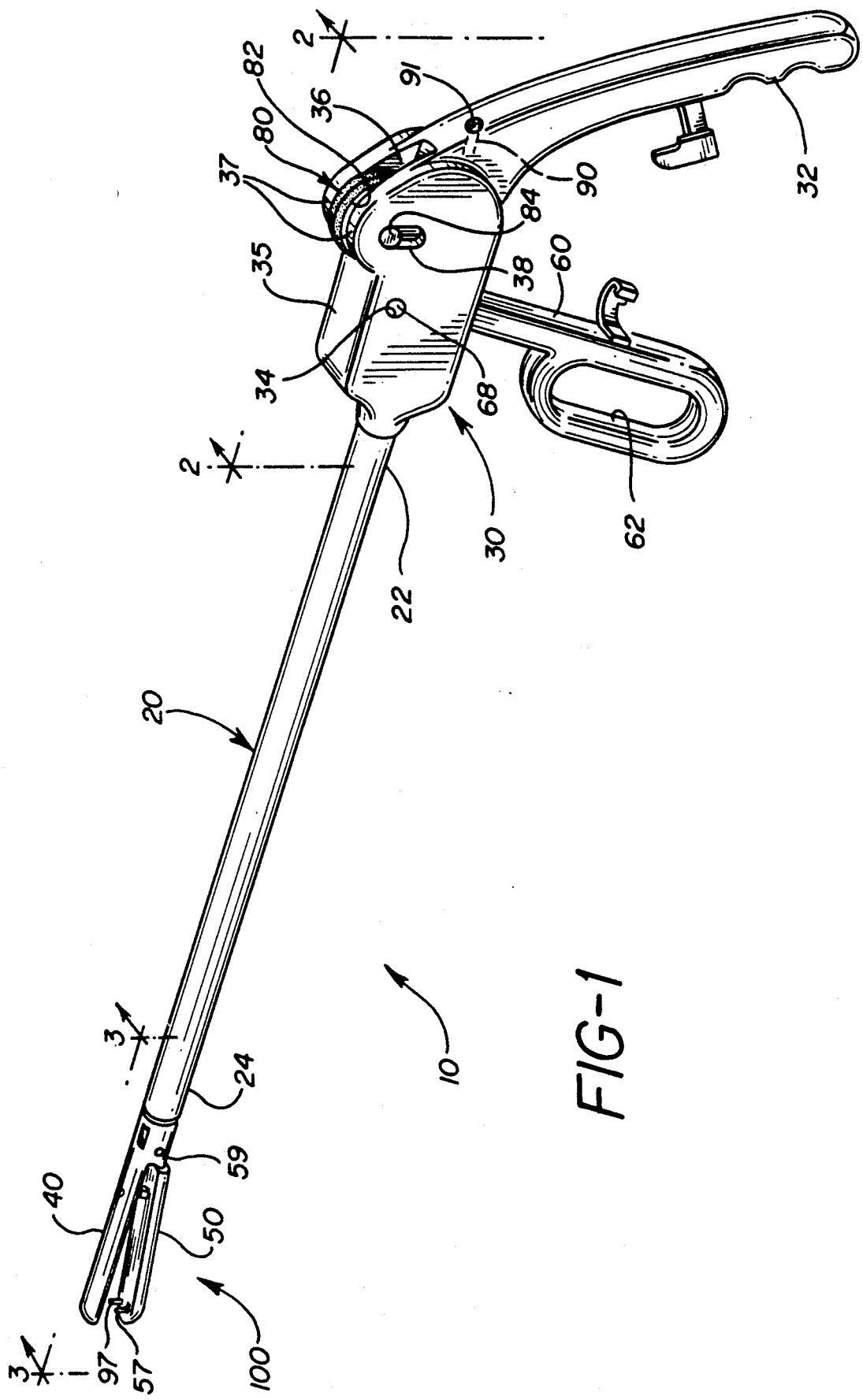
FIG. 1 is a perspective view of the endoscopic suture punch of the present invention.
Figure 2:
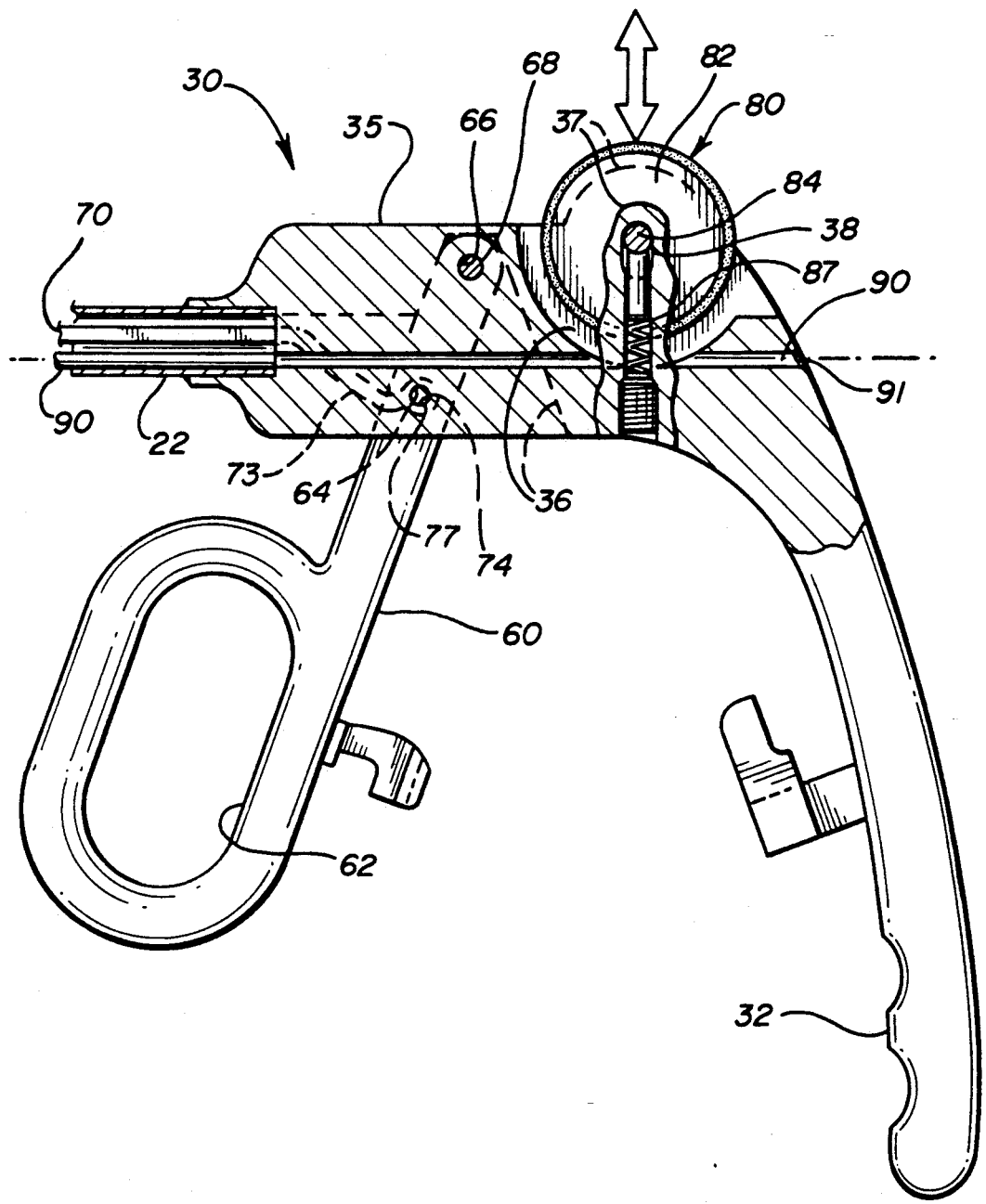
FIG. 2 is a partial cross-sectional view of the proximal end of endoscopic suture punch of the present invention as taken along View Line 2—2 of FIG. 1.
Figure 3:
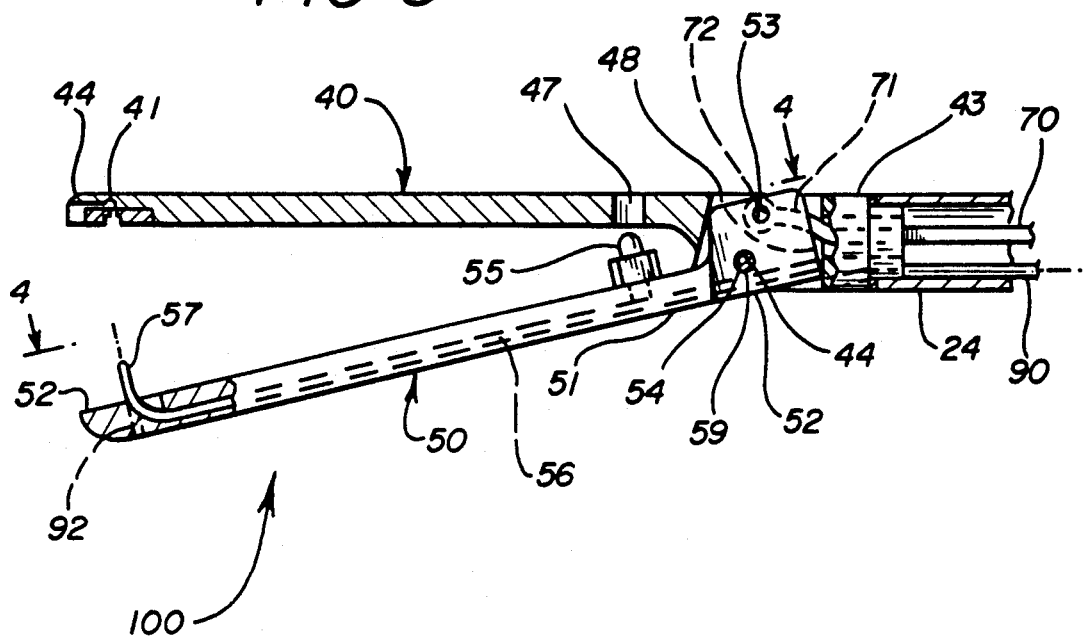
FIG. 3 is a partial cross-sectional view of the distal end of the endoscopic suture punch as taken along View Line 3—3 of FIG. 1.

The endoscopic suture punch 10 of the present invention is seen in FIGS. 1, 2 and 3. The suture punch 10 is seen to have elongated tubular frame 20 having proximal end 22 and distal end 24. The handle 30 is mounted to proximal end 22 of frame 20 and the jaws 100 are mounted to the distal end 24 of the tubular frame 20. The handle 30 is seen to have downwardly extending hand grip 32 and head portion 35 having cavity 36. Pivot holes 34 extend through head portion 35 on either side of cavity 36.

The tubular suture pathway means 90 is seen to extend axially through the handle 30 and the tubular frame 20. Entry port 91 is located in the upper proximal side of handle 30 and provides access to tubular suture pathway 90. The actuating lever 60 has lower extending D-shaped finger grip 62. The upper section of lever 60 has upper pivot holes 64 and 66. The actuating lever 60 is seen to be pivotally mounted in cavity 36 of handle head 35 by pin 68 which is inserted through pivot hole 66 and the pivot holes 34 in head portion 35. The actuating lever 60 and the handle 30 are seen to have conventional mating locking tabs 69 and 39 for locking the moveable jaw 50 in a closed position.

The actuating rod 70 is seen to have distal angulated end 71 with distal mounting hole 72 and proximal angulated end 73 with proximal mounting hole 74. The actuating rod 70 is pivotally mounted to actuating lever 60 by pin 77 inserted through pivot hole 64 and proximal mounting hole 74.

The handle head 35 is further seen to have upwardly extending semicircular, opposed tab members 37 having slots 38 therein for mounting suture drive wheel 80. Suture drive wheel 80 has disk member 82, rim 85 and perpendicular shaft 84 about which disk 82 rotates. The ends of shaft 84 are mounted in slots 38. Springs 87 mounted in handle head 35 provide an upward bias against the shaft 84 in slots 38. The wheel 80 and springs 87 and tab members 37 with slots 38 constitute the drive means for the suture punch 10. It will be appreciated by those skilled in the art that wheel 80 can be replaced with a cylinder or roller or other equivalent drive means. As described in more detail later herein, drive wheel 80 moves a suture through the suture pathway means of the suture punch 10. This is accomplished by applying downward pressure upon the wheel 80 until rim 85 contacts the suture. Then, wheel 80 is rotated by application of a torque to the wheel 80, thereby pushing the suture through the pathway means. It will be appreciated by those skilled in the art that the manual drive means may be powered by a conventional motor, e.g., electric or pneumatic or the like, mounted to the suture punch 10 and actuated by a conventional switch means. If desired, the motor may be coupled to a conventional power transmission (e.g., gear box or fluid transmission or belt transmission) which in turn powers the suture drive means.

Figure 4:
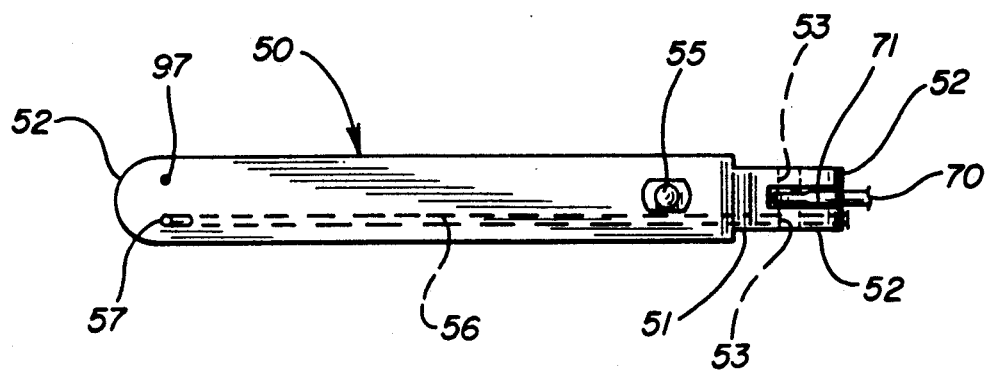
FIG. 4 is a plan view of the moveable jaw as seen along View Line 4—4 of FIG. 3.
Figure 7:
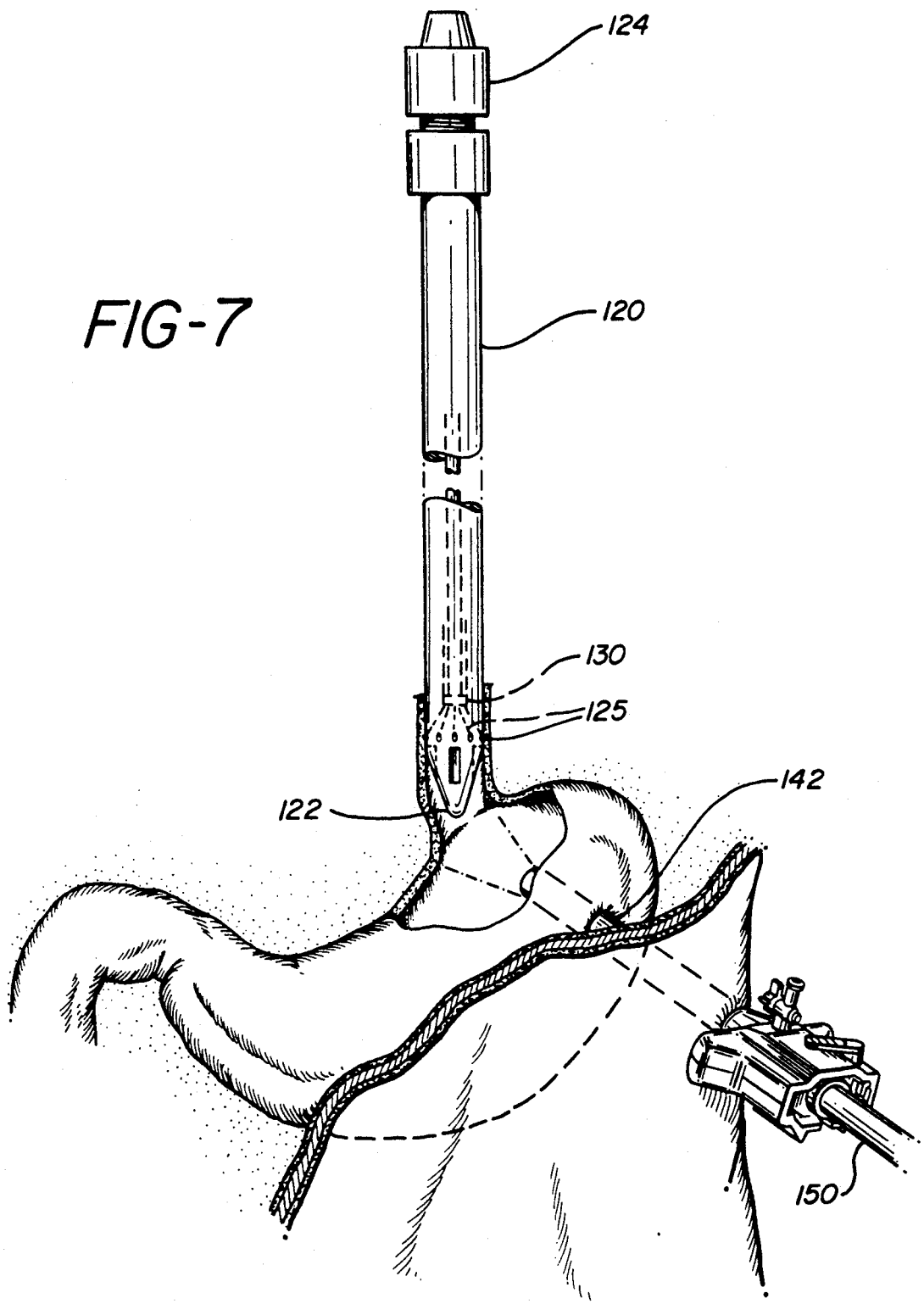
FIG. 7 is a perspective view showing the invaginator inserted in the distal end of the esophagus and also showing a trocar cannula with an endoscope inserted through the abdominal wall and stomach wall for viewing the surgery.
Figure 8:
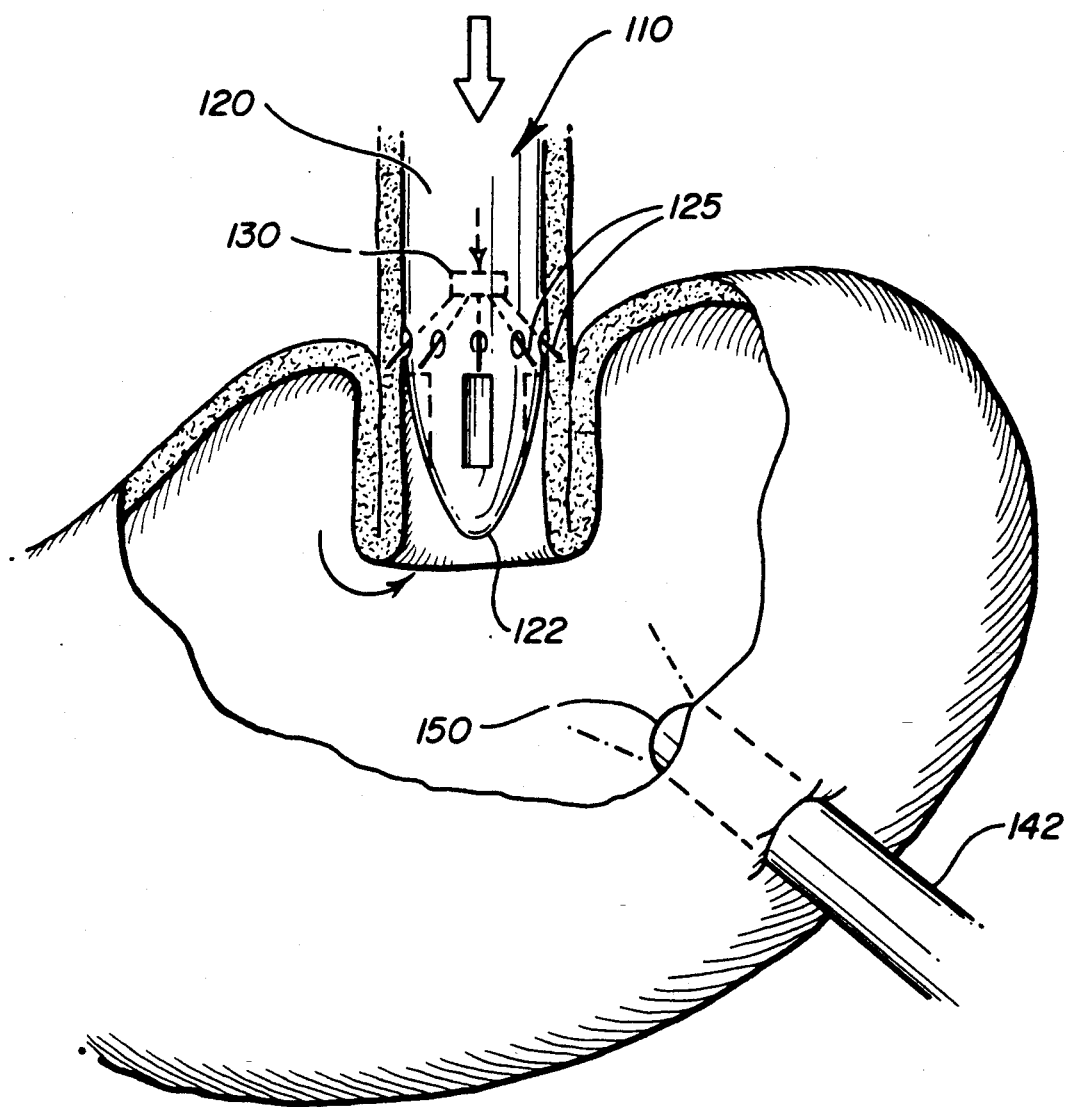
FIG. 8 is a perspective view of the invaginator with tissue engaging means actuated being pushed distally down the esophagus to form an invaginated fold within the stomach.
Figure 9:
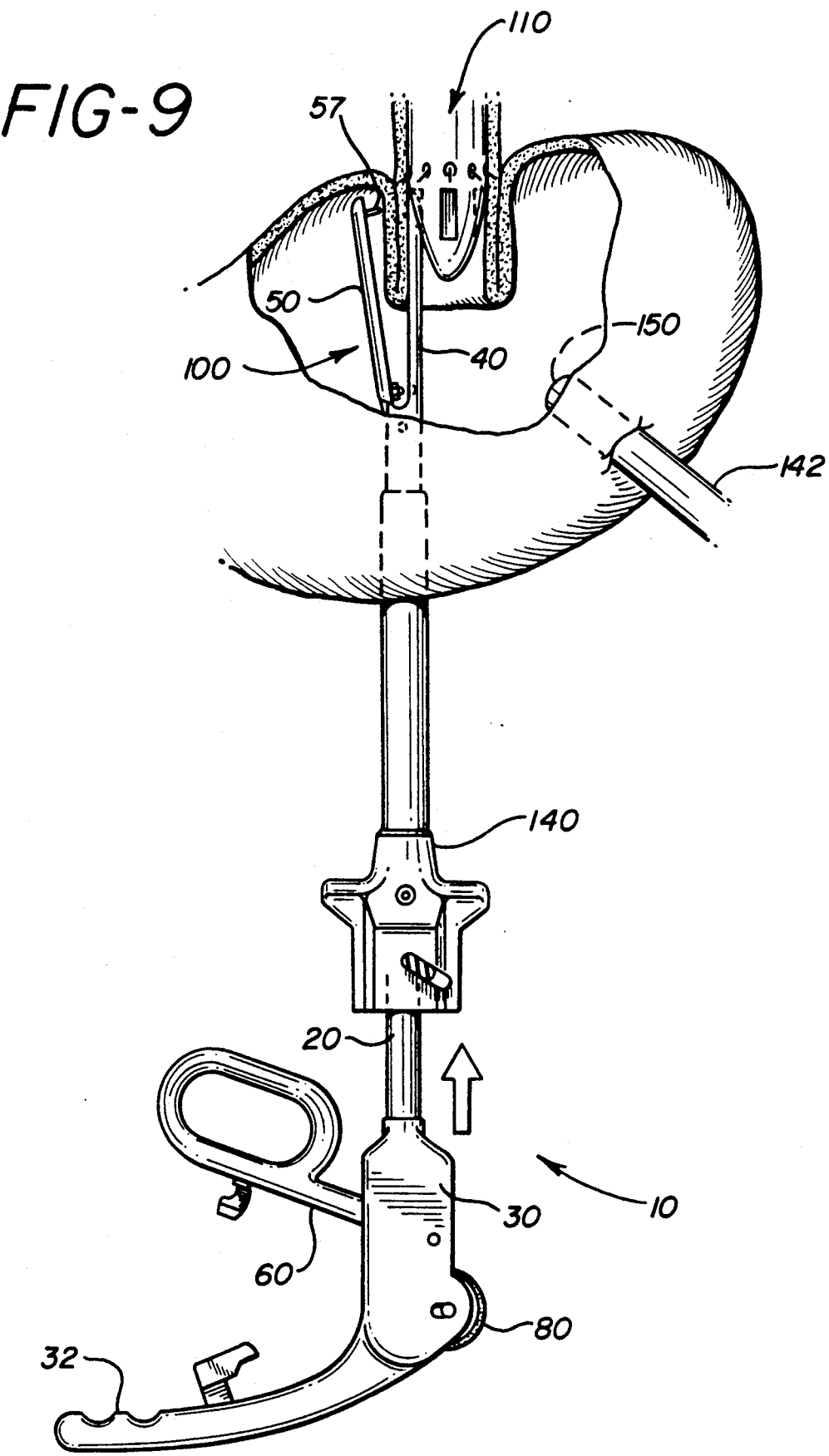
FIG. 9 is a perspective view showing the suture punch of the present invention inserted through a trocar cannula with the jaws placed about the invaginated fold prior to actuation of the jaws.
Figure 10:
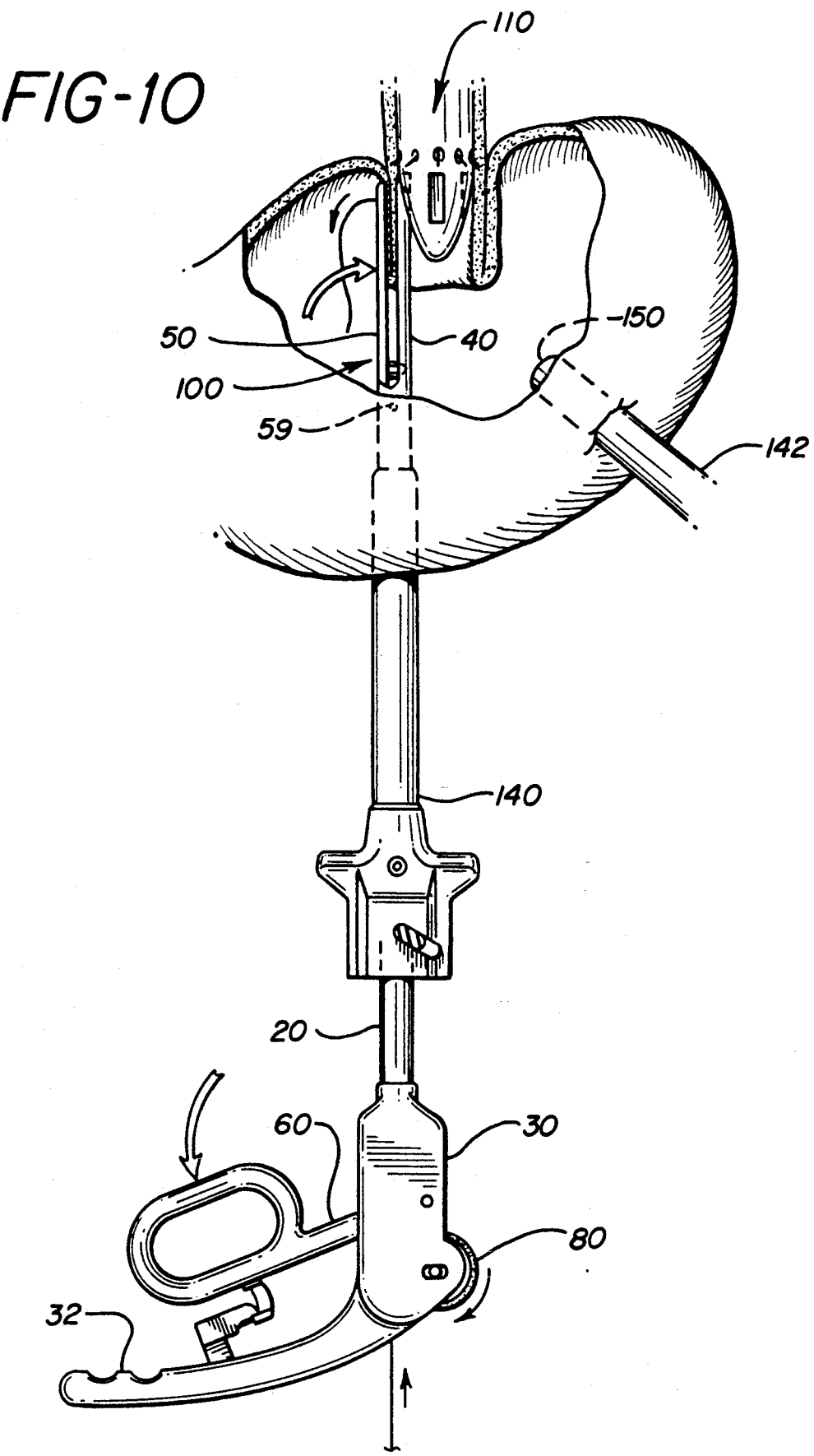
FIG. 10 is a perspective view showing the invaginator jaws actuated about the fold and a suture fed through the suture pathway through the invaginated fold and out through the jaws.

With reference to FIGS. 3 and 4, the jaws 100 are seen to consist of a stationary jaw 40 and a moveable or pivotally mounted movable jaw 50. The term moveable as used herein is defined to include hingingly and pivotally and other equivalent mounting methods. The stationary jaw 40 is seen to have cylindrical proximal mounting end 43 and pivot pin hole 44. Proximal mounting end 43 is mounted to the distal end 24 of tubular frame 20. Cavity 48 is seen to be contained in the proximal end of jaw 40 distal to proximal mounting end 43. Optional post receiving hole 47 is centrally located in jaw 40, distal to cavity 48, for receiving optional post 55. The distal end 44 of stationary member 40 is seen to have an arcuate pathway 41 for receiving a suture, as best seen in FIG. 6.

Moveable jaw 50 is seen to have at its proximal end 51 a pair of opposed mounting tabs 52 containing upper pivot holes 53 for mounting the distal end 71 of actuating rod 70. Lower pivot holes 54 are contained in the proximal end 51 of moveable jaw 50. Member 50 is pivotally mounted in stationary jaw 40 by mounting the proximal end 51 within the cavity 48 located in the proximal end 43 of stationary jaw 40 and inserting a pin 59 through pivot holes 54 and 44. If desired, both the jaws 100 may be moveable in which case the jaw 40 and jaw 50 would each be pivotally or movably mounted in a conventional manner to the distal end 24 of frame 20.

A tubular suture pathway 90 extends from the proximal end of handle 30 through the upper head cavity 35 and into the suture pathway 56 in movable jaw 50. Tubular pathway 56 is aligned with pathway 90 when moveable jaw 50 is in the actuated or closed position. Optionally, tubular pathway 56 is connected to pathway 90 using conventional tubing connecting means such as fittings, welding, brazing and the like. Moveable jaw 50 has a tubular pathway means 56 extending from the proximal end 51 and continuing to the distal end 52 of the movable jaw 50 where it curves upwardly to form a punch 57. It will be appreciated that when tubular pathway 56 is optionally connected to pathway 90, then tubular pathway 56 is sufficiently flexible to effectively allow bending without constricting the pathway when moveable jaw 50 is opened. Moveable jaw 50 also has tubular pathway 92 mounted opposite to punch 57. The distal end of pathway 92 extends upwardly to form punch 97. The proximal end 94 of pathway 92 exits the jaw 50 through port 99. The upper or distal tips of punch 57 and punch 97 are sufficiently sharp to effectively penetrate tissue. The piercing tips of punches 57 and 97 will typically have a piercing configuration conventional in this art. The proximal end of tubular pathway 90 is open partially in the vicinity of the wheel 80 so that the rim 85 of wheel 80 can engage and drive the suture through the tubular pathway 90 and through the tubular pathways 56 and 92 and the punches 57 and 97 in the movable jaw 50, and the pathway arcuate 41 in stationary jaw 40, and out through the exit port 99 in the movable jaw 50, as best seen in FIGS. 5 and 6. The suture pathway means of the endoscopic suture punch 10 consists of entry port 91, tubular pathway 90, tubular pathway 56, punch 57, arcuate pathway 41, punch 97, pathway 92 and exit port 99. The cross-section of the tubular pathway is preferably circular but may have other geometric configurations including and ellipse, polygon, square and rectangle. Although not shown in the drawings, if one were willing to accept the disadvantages, if any, pathway 92 may be extended proximally through the jaw 50, tubular frame 20, and handle 30 to an exit port in handle 30 so that the suture exits form handle 30 rather than through jaw 50. In addition, as previously mentioned, jaws 40 and 50 may both be moveable if so desired. This is accomplished in a conventional manner wherein jaw 40 is pivotally mounted to the distal end 24 of frame 20 using conventional mounting techniques. The distal end 71 of actuating rod 70 would then be pivotally mounted, either directly or indirectly, to the jaws 100.

The sutures which may be used with the endoscopic suture punch 10 may comprise conventional surgical sutures having sufficient flexibility to effectively move through and about the suture pathway, particularly the curved sections of the pathway. The sutures may be absorbable or nonabsorbable, monofilament or multifilament and include sutures manufactured by ETHICON, Inc., Somerville, N.J.

A tissue invaginator 110 is seen in FIGS. 7, 8, 9, and 10. The tissue invaginator is seen to have an elongate member 120 having a tapered, blunt distal end 122. The invaginator 110 has tissue engaging means 125 consisting of a plurality of needles which, when actuated, extend outwardly and downwardly. The needles are contained within member 120 when not actuated. The invaginator 110 also has actuating means 130 for actuating or deactuating the tissue engaging means such that the needles are either extended for invagination or withdrawn for insertion removal into and out of the esophagus.

The suture punch 10 and invaginator 110 of the present invention are used in the following manner to perform an anti-reflux procedure as seen in FIGS. 7, 8, 9, 10, and 11. Using conventional endoscopic procedures, at least one trocar 140, having a piercing obturator concentrically housed in a trocar cannula 142, is inserted through the abdominal wall of a mammal, and then through the stomach wall into the interior of the stomach. The conventional trocar obturator is removed leaving a trocar cannula pathway to the stomach. An endoscope 150 is inserted through another trocar cannula 142 into the stomach. The output of the endoscope 150 is typically displayed on a video monitor. Next the invaginator 110 is inserted into the patient's esophagus. When the surgeon observes (on the video monitor connected to the endoscope) the distal end 122 of the invaginator 110 protrude through the opening of the esophagus into the stomach, the surgeon actuates the actuating mechanism on the invaginator 110 causing the tissue engaging means 125 to be extended and engage the tissue of the lower esophagus. The surgeon then pushes down on the proximal end 124 of the invaginator 110 displacing the invaginator 110 distally thereby causing the upper part of the stomach to form an invaginated fold about the invaginator 110. The surgeon then inserts the jaws 100 of the suture punch 10 through the trocar cannula and positions the jaws 40 and 50 of the suture punch 10 within the stomach proximal to the invaginated fold. With the jaws 40 and 50 in the open position, the surgeon inserts the jaw 40 between the invaginator 110 and the esophageal side of the invaginated fold, while the jaw 50 is located on the stomach side of the invaginated fold. Then the surgeon actuates the actuating mechanism of the suture punch 10 by pulling back on the actuating lever 60 which causes actuating rod 70 to close moveable jaw 50 by forcing it to pivot about the pin 59. This causes the punch 57 and 97 to punch a pathway through the tissue of the invaginated fold. Locking tabs 39 and 69 lock the jaws in a closed position. Then the surgeon threads a conventional suture into the entrance hole 91 and through the pathway 90, moving the suture through the pathway 90 by engaging the suture with rim 85 of the wheel 80 by rotating the wheel 80 in a clockwise manner while pressing down on the wheel 80. The suture exits the distal end of the pathway 90 and then enters the tubular pathway 56 contained within the moveable jaw 50 and moves through punch 57 thereby passing through the inverted tissue. The suture then enters pathway 41 in stationary jaw 40 and then enters punch 97 thereby again passing through the inverted tissue and next enters pathway 92. The suture then exits pathway 92 through exit hole 99 contained in moveable jaw 50. The surgeon feeds a sufficient amount of suture through the suture punch 10 so that a free end is available for removal through the trocar cannula. The surgeon then deactivates the jaws 100 by pushing lever 60 forward after disengaging locking tabs 39 and 69. As the jaws 100 open, the punches 57 and 97 are withdrawn from the tissue, leaving the suture in the tissue pathway formed by punches 57 and 97. The suture in the tissue has a resultant U-stitch configuration. Also, after the jaws 100 are opened, additional suture is fed out through the punch 57 to create sufficient slack in the suture to allow removal of suture punch 10 without applying tension to the esophageal tissue. This free end of the suture is then grasped as the suture punch 10 is removed through the trocar cannula along with the other end of the suture so that two free ends of the suture are external to the cannula. As mentioned previously, the suture in the tissue has a U-stitch configuration. Then, an extracorporeal knot is tied which is then pushed down the trocar cannula and secured in place at the invaginated fold using conventional knot pushing techniques. This procedure is repeated until the surgeon has emplaced a sufficient number of sutures effective to adequately retain the fold in its invaginated position as seen in FIG. 12. Then the surgeon withdraws the invaginator 110 by deactivating the tissue engaging means 125 and pulling the invaginator 110 proximally out through the esophagus. Next, the surgeon withdraws the trocar cannulas 142 and closes the incisions in accordance with conventional endoscopic procedures by applying sutures, staples and/or tape. In place of the conventional trocar 140 and trocar cannula 142, a specially configured cannula may be used to introduce a pathway to the stomach. The specially configured cannula has an insufflation port, a skin flange and inflatable balloon. This cannula is disclosed in U.S. Pat. No. 5,088,979 which is incorporated by reference.

It will be noted that although an endoscopic method has been described for use of the suture punch and invaginator in the anti-reflux procedure, the procedure can also be used with open surgical techniques wherein a radical open incision is made through the abdominal wall and wall of the stomach and the suture punch is inserted through this incision as opposed to using an endoscopic procedure which utilizes trocar cannulas.

The endoscopic suture punch 10 of the present invention can be used in many endoscopic surgical procedures, including those previously described herein, where there is a need to perform suturing. The endoscopic suture punch 10 is not limited to use with an endoscopic anti-reflux procedure.

The endoscopic suture punch 10 of the present invention will be constructed from materials conventional in this art. The materials include plastics such as polycarbonate, nylon, polyetherimide and nitrile as well as the 300 and 400 series stainless steels and the like and equivalents thereof. The tips of the punches 57 and 97 will be manufactured using conventional sharpening methods including grinding with conventional grinding apparatus and the like. The suture punch 10 is typically packaged in conventional packaging materials. The suture punch 10 is typically sterilized after packaging and prior to use using conventional sterilization techniques. It is particularly preferred to sterilize the apparatus 10 using cobalt-60 generated radiation, although other types of sterilization including autoclaving and ethylene oxide sterilization may be used.

The suture punch apparatus 10 may be used in conventional endoscopic techniques including cholecystectomy, appendectomy, anastomosis, hernia repair and the like. Endoscopic surgical techniques and procedures are widely known, e.g., endoscopic surgical techniques are disclosed in the following publications which are incorporated by reference: *Textbook of Laparoscopy,* Jaroslav Hulka, M.D., Grune & Stratton, Inc., New York (1985) and *Laparoscopy for Surgeons,* Barry A. Salky, M.D., Igaku-Shoin, New York (1990). When utilizing endosurgical techniques, initially a patient is typically anesthetized using a sufficient dose of anesthesia effective to induce an anesthetized state. Conventional anesthesiology techniques and procedures are utilized including, where needed, the use of an endotracheal tube and a ventilator. The next step after the application of anesthesia is the insufflation of the body cavity containing the target surgical site. This is done using conventional techniques and equipment. The gases which are typically used for insufflation include conventional sterile gases such as carbon dioxide and the like. After the body cavity has been insufflated sufficiently so that the surgeon has room to effectively manipulate and maneuver instrumentation within the body cavity, several conventional trocars are inserted in a conventional manner through the body cavity wall into the body cavity, for example, the abdominal cavity. Conventional trocars typically comprise a piercing obturator concentrically housed in a trocar cannula. After the trocars are inserted, the piercing obturators are then removed from the trocar cannulas leaving the trocar cannulas as pathways to the body cavity. Conventional endoscopic instrumentation is inserted through the cannulas including endoscopes, staplers, sutures, cannulas, electrosurgical instruments, ligating clip appliers, and the like. The instruments are maneuvered to the target surgical site where a surgical procedure is performed. The surgeon views the interior of the body cavity and the target surgical site by observing the output from the endoscope. Conventional endoscopes typically are connected to video cameras and the output displayed on a video monitor.

Figure 11:
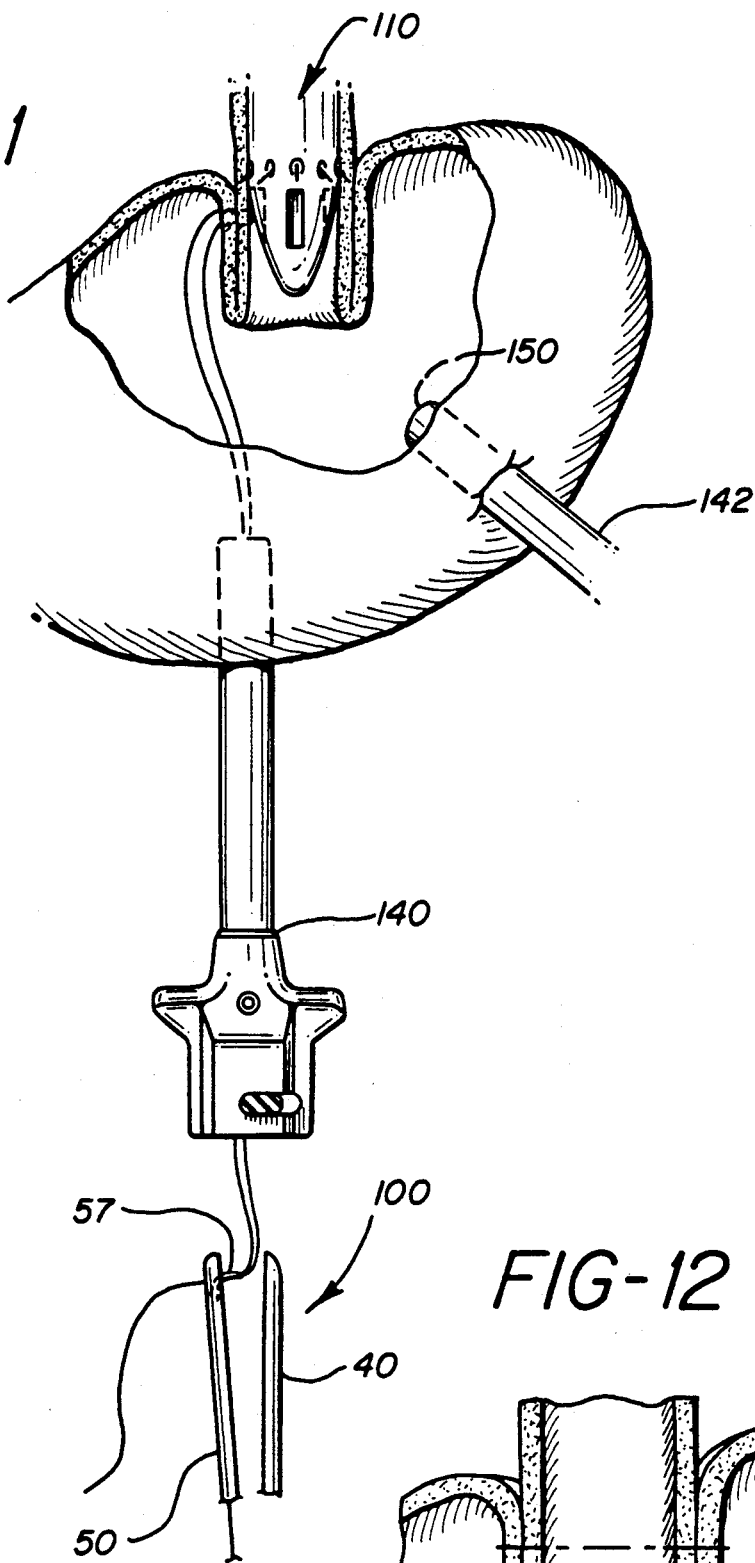
FIG. 11 is a perspective view showing the suture punch removed from the stomach and out from the trocar cannula with a suture loop in the invaginated fold and the ends of the suture exterior to the trocar.
Figure 12:
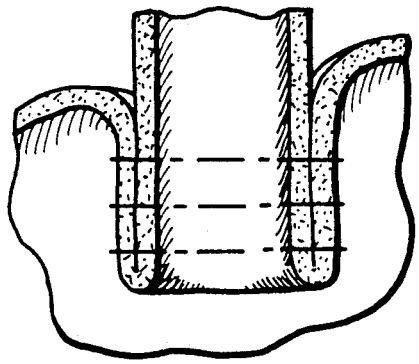
FIG. 12 is a partial cross-sectional view of the sutured, invaginated esophagus after completion of the anti-reflux procedure.

The suture punch 10 of the present invention produces a U-stitch configured suture in tissue as can be seen in FIGS. 11 and 12. The punches 57 and 97 punch or pierce tissue pathways in tissue. Typically, tissue which is to be sutured can be described as having a front and back side. A suture is emplaced through the pathway created by punch 57 and out through the back side of the tissue. The suture is then emplaced about and upon the back side of the tissue. The suture is then emplaced into the tissue pathway created by punch 97 and out of the front side of the tissue, thereby resulting in a U-stitch being emplaced in the tissue wherein the suture has a U-shaped configuration.

The following example is illustrative of the principles and practice of the present invention although not limited thereto.

EXAMPLE

A mammal is prepared for surgery using conventional surgical techniques. A sufficient dose of a conventional anesthesia is administered using conventional anesthesiology techniques effective to induce an anesthetized state. The abdominal cavity of the patient is then sufficiently insufflated using conventional insufflation equipment and techniques with carbon dioxide gas to produce an effective pneumoperitoneum. Three trocars are then inserted through the abdominal wall of the mammal into the abdominal cavity. The trocars are conventional trocars having elongated obturators with piercing tips concentrically housed in trocar cannulas. The trocar obturators are then removed leaving the trocar cannulas as pathways to the abdominal cavity. An endoscope is inserted through one of the trocar cannulas. The output from the endoscope is displayed on a video monitor. The surgeon observes the interior of the abdominal cavity on the video monitor and maneuvers instruments into position using the video monitor display. The endoscopic suture punch 10 of the present invention is inserted through one of the trocar cannulas. The surgeon maneuvers the distal end of the punch 10 to a position proximate to a target tissue site which is to be sutured. With the jaws 40 and 50 in the open position, the surgeon inserts the jaws 100 about the target tissue. Then the surgeon actuates the actuating mechanism of the suture punch 10 by pulling back on the actuating lever 60 which causes actuating rod 70 to close moveable jaw 50 by forcing it to pivot about the pin 59. This causes the punches 57 and 97 to punch a pathway through the target tissue. Locking tabs 39 and 69 lock the jaws in a closed position. Then the surgeon threads a conventional suture into the entrance hole 91 and through the pathway 90, moving the suture through the pathway 90 by engaging the suture with rim 85 of the wheel 80 by rotating the wheel 80 in a clockwise manner while pressing down on the wheel 80. The suture exits the distal end of the pathway 90 and then enters the tubular pathway 56 contained within the moveable jaw 50 and moves through punch 57. The suture then enters pathway 41 in stationary jaw 40 and then enters punch 97 and next enters pathway 92. The suture then exits pathway 92 through exit hole 99 contained in moveable jaw 50. The surgeon feeds a sufficient amount of suture through the suture punch 10 so that a free end is available for removal through the trocar cannula. The surgeon then releases locking tabs 39 and 69 and deactivates the jaws 100 by pushing lever 60 forward. This causes the jaws 100 to open and the punches 57 and 97 to be removed from the tissue, leaving the suture in the tissue pathway formed by punches 57 and 97. Additional suture is then fed out of punch 57 to allow the punch 10 to be removed without stressing the tissue. This free end of the suture is then grasped as the suture punch 10 is removed through the trocar cannula along with the other end of the suture so that two free ends of the suture are external to the cannula. The suture in the tissue has a resultant U-stitch configuration. Then, an extracorporeal knot is tied which is then pushed down the trocar cannula and secured in place at the target tissue site using conventional knot pushing techniques. This procedure is repeated until the surgeon has emplaced a sufficient number of sutures effective to adequately suture the target tissue. The surgeon then withdraws the distal end of the punch 10 from the body cavity and out through the trocar cannula. The surgeon then removes the trocar cannulas and closes up the wounds using conventional techniques including stapling, suturing, and/or taping.

Although this invention has been shown and described with respect to detailed embodiments thereof, it will be understood by those skilled in the art that various changes in form and detail thereof may be made without the departing from the spirit and scope of the claimed invention.

What is claimed is:

1. An endoscopic suture punch, comprising:
   an elongate tubular frame;
   a handle mounted to an end of said frame;
   a pair of jaws mounted to the other end of said frame, wherein one jaw is movable, and one jaw is stationary, said movable jaw being pivotally mounted;
   actuation means mounted to said frame for actuating at least one jaw wherein the actuation means comprises a lever pivotally mounted in the handle and an actuation rod pivotally connected to the lever on one end and to at least one jaw on the other end;
   punch means mounted to at least one of said jaws for punching a pathway through tissue;
   a suture pathway means through said handle, frame, jaws and punch means for receiving a suture;
   wherein the suture pathway means comprises a first tubular member extending through the handle, frame, and a first jaw, a second tubular member extending through said first jaw and an arcuate pathway in the other jaw said arcuate pathway connecting the first and second tubular members; and
   suture drive means mounted to said handle for moving a suture through the pathway means.

2. The suture punch of claim 1 comprising an entrance port for the suture pathway in the handle and an exit port in the handle.

3. The suture punch of claim 1 wherein the suture punch comprises an entrance port for the suture pathway in the handle and an exit port in one jaw.

4. The suture punch of claim 1 wherein the suture drive means comprises a wheel having a rim and an axial shaft mounted to the center thereof, said wheel rotatably mounted to the handle for engaging a suture and pushing the suture through the suture pathway means.

5. The suture punch of claim 4 wherein the handle comprises an upper head having a cavity therein and a pair of upwardly extending tabs on either side of said cavity having slots, wherein the wheel is mounted in said cavity and shaft is mounted in said slots.

6. The suture punch of claim 5 further comprising biasing means for biasing the wheel upward in the slots of the tab members.

7. The suture punch of claim 1 wherein both jaws are movably mounted.

8. The suture punch of claim 1 additionally comprising
   a motor mounted to the handle;
   means for coupling the motor to the suture drive means; and
   actuation means for activating and deactivating the motor.

9. The suture punch of claim 1 wherein the punch means comprises sections of the tubular members extending upwardly from one jaw to form punches, said punches having sharpened piercing tips effective to pierce tissue.

10. A combination comprising an endoscopic suture punch and an invaginator for performing an anti-reflux procedure, wherein the invaginator comprises;
    an elongate member having a tapered, blunt distal end;
    tissue engaging means extending from said member and mounted to said member proximal to said distal end; and,
    actuating means for actuating said tissue engaging means; and,
    wherein said endoscopic suture punch comprises;
    an elongate tubular frame;
    a handle mounted to one end of said frame;
    a pair of jaws mounted to the other end of said frame, wherein one jaw is moveable, and one jaw is stationary, said moveable jaw being pivotally mounted;
    actuation means mounted to said frame for actuating at least one jaw wherein the actuation means comprises a lever pivotally mounted in the handle and an actuation rod pivotally connected to the lever on one end and to at least one jaw on the other end;

punch means attached to at least one of said jaws for punching a pathway through tissue;

a suture pathway means through said frame, handle, jaws and punch means for receiving a suture wherein the suture pathway comprises a first tubular member extending through the handle, frame, and a first jaw, a second tubular member extending through said first jaw, and an arcuate pathway in the other jaw, said arcuate pathway connecting the first and second tubular members; and, suture drive means mounted to the handle for moving a suture through the pathway means.

11. The suture punch of claim 10 comprising an entrance port for the suture pathway in the handle and an exit port in the handle.

12. The suture punch of claim 10 wherein the suture punch comprises an entrance port for the suture pathway in the handle and an exit port in one jaw.

13. The suture punch of claim 10 wherein the suture drive means comprises a wheel having a rim and an axial shaft mounted to the center thereof, said wheel rotatably mounted to the handle for engaging a suture and pushing the suture through the suture pathway means.

14. The suture punch of claim 10 wherein the handle comprises an upper head having a cavity therein an a pair of upwardly extending tabs on either side of said cavity having slots wherein the wheel is mounted in said cavity and shaft is mounted in said slots.

15. The suture punch of claim 14 further comprising biasing means for biasing the wheel upward in the slots of the tab members.

16. The suture punch of claim 10 wherein both jaws are movably mounted.

17. The suture punch of claim 10 additionally comprising
a motor mounted to the handle;
means for coupling the motor to the suture drive means; and
actuation means for activating and deactivating the motor.

18. The suture punch of claim 10 wherein the punch means comprises sections of the tubular members extending upwardly from one jaw to form punches, said punches having sharpened piercing tips effective to pierce tissue.

19. A method of performing an anti-reflux procedure in a mammal, comprising:
A) inserting an invaginator into the esophagus of the mammal wherein the invaginator comprises:
an elongate member having a distal end;
tissue engaging means extendable from said member and attached to said member proximal to said distal end; and,
actuating means for actuating said tissue engaging means;
actuating the actuating means to engage the distal end of the esophagus;
B) displacing the invaginator and the tissue distally into the stomach to form an invaginated fold about the invaginator;
C) inserting an endoscopic suture punch into the stomach proximal to the distal end of the invaginator, wherein the endoscopic suture punch comprises;
an elongate tubular frame;
a handle mounted to one end of frame;
a pair of jaws mounted to the other end of said frame, wherein one jaw is movable and one jaw is stationary, said movable jaw being pivotably mounted;
actuation means mounted to said frame for actuating at least one jaw wherein the actuation means comprises a lever pivotally mounted in the handle and an actuation rod pivotally connected to the lever on one end and to at least one jaw on the other end;
punch means mounted to at least one jaw of punching a pathway through tissue;
a suture pathway through said frame, handle, jaws and punch means for receiving a suture, wherein the suture pathway comprises a first tubular member extending through the handle, frame, and first jaw, a second tubular member extending through said first jaw and an arcuate pathway in the outer jaw said arcuate pathway connecting the first and second tubular members; and,
suture drive means mounted to said handle for moving a suture through the pathway means;
D) suturing the invaginated fold by inserting the open jaws of punch about the invaginated fold;
E) closing the jaws about the fold such that the punch means punch a pathway thorough the tissue of the fold;
F) moving a suture through the suture punch pathway through the invaginated fold and out through the endoscopic suture punch by engaging the suture drive means; and,
G) securing a knot in the suture about the invaginated fold.

20. The suture punch of claim 19 comprising an entrance port for the suture pathway in the handle and an exit port in the handle.

21. The suture punch of claim 19 wherein the suture punch comprises an entrance port for the suture pathway in the handle and an exit port in one jaw.

22. The suture punch of claim 29 wherein the suture drive means comprises a wheel having a rim and an axial shaft mounted to the center thereof, said wheel rotatably mounted to the handle for engaging a suture and pushing the suture through the suture pathway means.

23. The suture punch of claim 19 wherein the handle comprises an upper head having a cavity therein and a pair of upwardly extending tabs on either side of said cavity having slots wherein the wheel is mounted in said cavity and shaft is mounted in said slots.

24. The suture punch of claim 23 further comprising biasing means for biasing the wheel upward in the slots of the tab members.

25. The suture punch of claim 19 wherein both jaws are movably mounted.

26. The suture punch of claim 19 further comprising
a motor mounted to the handle;
means for coupling the motor to the suture drive means; and
actuation means for activating and deactivating the motor.

27. The suture punch of claim 19 wherein the punch means comprises sections of the tubular members extending upwardly form one jaw to form punches, aid punches having sharpened piercing tips effective to pierce tissue.

28. A method of endoscopic suturing comprising:

A) inserting an endoscopic suture punch into a body cavity though a trocar cannula, wherein the endoscopic suture punch comprises:
an elongate tubular frame;
a handle mounted to one end of frame;
a pair of jaws mounted to the other end of said frame, wherein one jaw is movable and one jaw is stationary, said movable jaw being pivotally mounted;
actuation means attached to said frame for actuating at least one jaw, wherein the actuation means comprise a lever pivotally mounted in the handle and an actuation rod pivotally connected to the lever on one end and to at least one jaw to the other end;
punch means mounted to at least one jaw for punching a pathway through tissue;
a suture pathway through said frame, handle, jaws and punch means for receiving a suture, wherein the suture pathway comprises a first tubular member extending through the handle, frame, and first jaw, a second tubular member extending through said first jaw and an arcuate pathway in the other jaw, said arcuate pathway connecting the first and second tubular members
suture drive means mounted to said handle for moving a suture through the pathway means;
B) opening the jaws of the punch;
C) placing the open jaws of punch about tissue;
D) closing the jaws about the tissue such that the punch means pierce a pathway thorough the tissue;
E) moving a suture through the suture punch pathway through the tissue and out through the endoscopic suture punch by engaging the suture drive means; and,
F) securing a knot in the suture about the tissue.

29. The suture punch of claim 28 comprising an entrance port for the suture pathway in the handle and an exit part in the handle.

30. The suture punch of claim 28 wherein the suture punch comprises an entrance port for the suture pathway in the handle and an exit port in one jaw.

31. The suture punch of claim 28 wherein the suture drive means comprises a wheel having a rim and an axial shaft mounted to the center thereof, said wheel rotatably mounted to the handle for engaging a suture and pushing the suture through the suture pathway means.

32. The suture punch of claim 31 wherein the handle comprises an upper head having a cavity therein and a pair of upwardly extending tabs on either side of said cavity having slots wherein the wheel is mounted in said cavity and shaft is mounted in said slots.

33. The suture punch of claim 32 further comprising biasing means for biasing the wheel upward in the slots of the tab members.

34. The suture punch of claim 28 wherein both jaws are movably mounted.

35. The suture punch of claim 28 comprising
a motor mounted to the handle;
means for coupling the motor to the suture drive means; and
actuation means for activating and deactivating the motor.

36. The suture punch of claim 28 wherein the punch means comprises sections of the tubular members extending upwardly form one jaw to form punches, said punches having sharpened piercing tips effective to pierce tissue.

37. The suture punch of claims 1, 4, 19, or 28 wherein the suture pathway means produces a stitch in tissue having a U-shaped configuration.

* * * * *

UNITED STATES PATENT AND TRADEMARK OFFICE
CERTIFICATE OF CORRECTION

PATENT NO. : 5,254,126
DATED : October 19, 1993
INVENTOR(S) : Charles J. Filipi, et al It is certified that error appears in the above-indentified patent and that said Letters Patent is hereby corrected as shown below:

Column 12, line 41, (claim 22) "claim 29" should read --claim 19--.
Column 12, line 65, (claim 27) "aid" should read --said--.

Signed and Sealed this

Twentieth Day of September, 1994

Attest:

BRUCE LEHMAN

Attesting Officer    Commissioner of Patents and Trademarks